US006608680B2

(12) United States Patent
Basiji et al.

(10) Patent No.: US 6,608,680 B2
(45) Date of Patent: Aug. 19, 2003

(54) TDI IMAGING SYSTEM FOR KINETIC STUDIES

(75) Inventors: David A. Basiji, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 161 days.

(21) Appl. No.: 09/932,838

(22) Filed: Aug. 17, 2001

(65) Prior Publication Data

US 2002/0047896 A1 Apr. 25, 2002

Related U.S. Application Data

(60) Provisional application No. 60/228,079, filed on Aug. 25, 2000.

(51) Int. Cl.[7] ............................................. G01N 21/00
(52) U.S. Cl. ........................... 356/338; 356/73; 356/344
(58) Field of Search ................................ 356/364, 338, 356/344, 73, 327, 326

(56) References Cited

U.S. PATENT DOCUMENTS

| | | | | |
|---|---|---|---|---|
| 4,786,165 | A | 11/1988 | Yamamoto et al. ............ 356/23 |
| 5,159,397 | A | 10/1992 | Kosaka et al. ................. 356/73 |
| 5,159,398 | A | 10/1992 | Maekawa et al. .............. 356/73 |
| 5,159,642 | A | 10/1992 | Kosaka ........................... 382/6 |
| 5,247,339 | A | 9/1993 | Ogino ........................... 356/73 |
| 5,272,354 | A | 12/1993 | Kosaka ........................ 250/574 |
| 5,422,712 | A | 6/1995 | Ogino ........................... 356/73 |
| 5,444,527 | A | 8/1995 | Kosaka ........................... 356/73 |
| 5,471,294 | A | 11/1995 | Ogino ........................... 356/73 |
| 5,548,395 | A | 8/1996 | Kosaka ........................... 356/73 |
| 5,596,401 | A | 1/1997 | Kusuzawa ...................... 356/23 |
| 5,633,503 | A | 5/1997 | Kosaka ...................... 250/458.1 |
| 5,644,388 | A | 7/1997 | Maekawa et al. .............. 356/73 |
| 5,674,743 | A | 10/1997 | Ulmer ...................... 435/287.2 |
| 5,754,291 | A | 5/1998 | Kain ............................ 356/338 |
| 5,760,899 | A | * 6/1998 | Eismann ...................... 356/326 |
| RE35,868 | E | 8/1998 | Kosaka ........................ 250/574 |
| 5,831,723 | A | 11/1998 | Kubota et al. ................. 356/73 |
| 5,848,123 | A | * 12/1998 | Strommer ................... 378/98.8 |
| 6,249,341 | B1 | * 6/2001 | Basiji et al. ................... 356/73 |
| 6,256,096 | B1 | * 7/2001 | Johnson ........................ 356/335 |

FOREIGN PATENT DOCUMENTS

WO     WO 00/42412     7/2000     .......... G01N/15/02

OTHER PUBLICATIONS

Ong, S.–H.; Horne, D.; Yeung, C.–K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11–15, 1985. pp. 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

* cited by examiner

*Primary Examiner*—Frank G. Font
*Assistant Examiner*—Layla Lauchman
(74) *Attorney, Agent, or Firm*—Ronald M. Anderson

(57) ABSTRACT

Light from an object such as a cell moving through an imaging system is collected, and imaged onto a time delay integration (TDI) detector, producing a pixelated output signal in response to the image of the object. The light can be emitted from a luminous object, from a source and scattered by the object, or can be a fluorescent emission by one or more object probes. Light absorbed or reflected by the object can also produce images for determining specific characteristics of the object. In one set of embodiments, the movement of the object is synchronized with that of the pixelated output signal, which is controlled by the readout rate of the TDI detector. Alternatively, the readout rate of the pixelated output signal is not synchronized with the movement of the object, thereby permitting multiple signals to be produced for each of a plurality of objects over time.

33 Claims, 7 Drawing Sheets

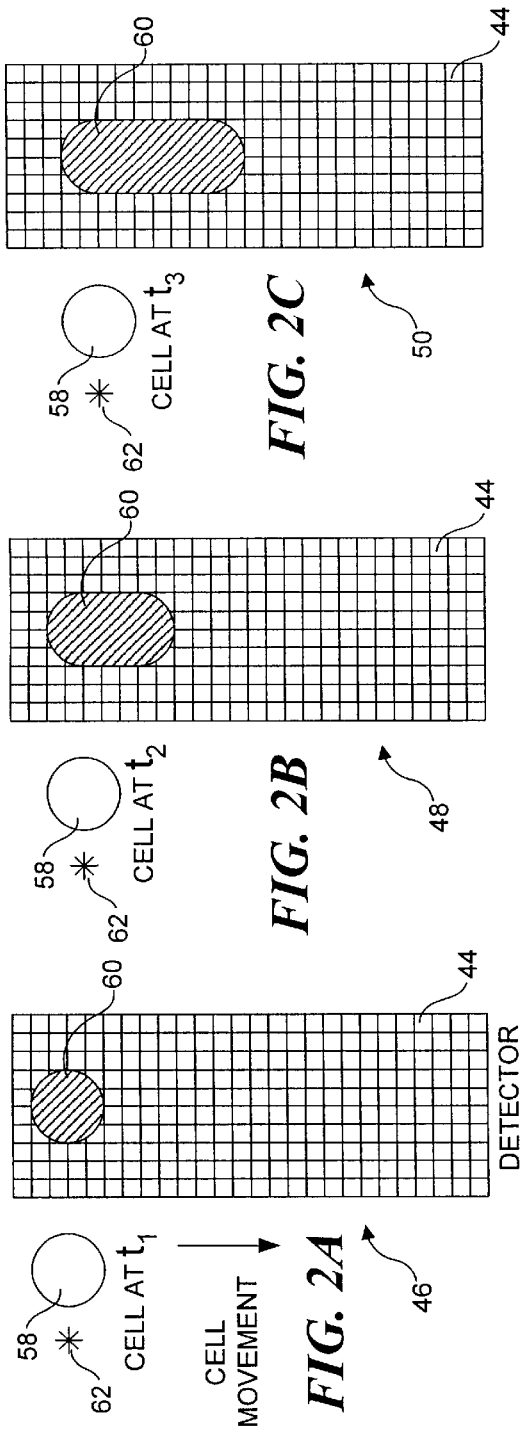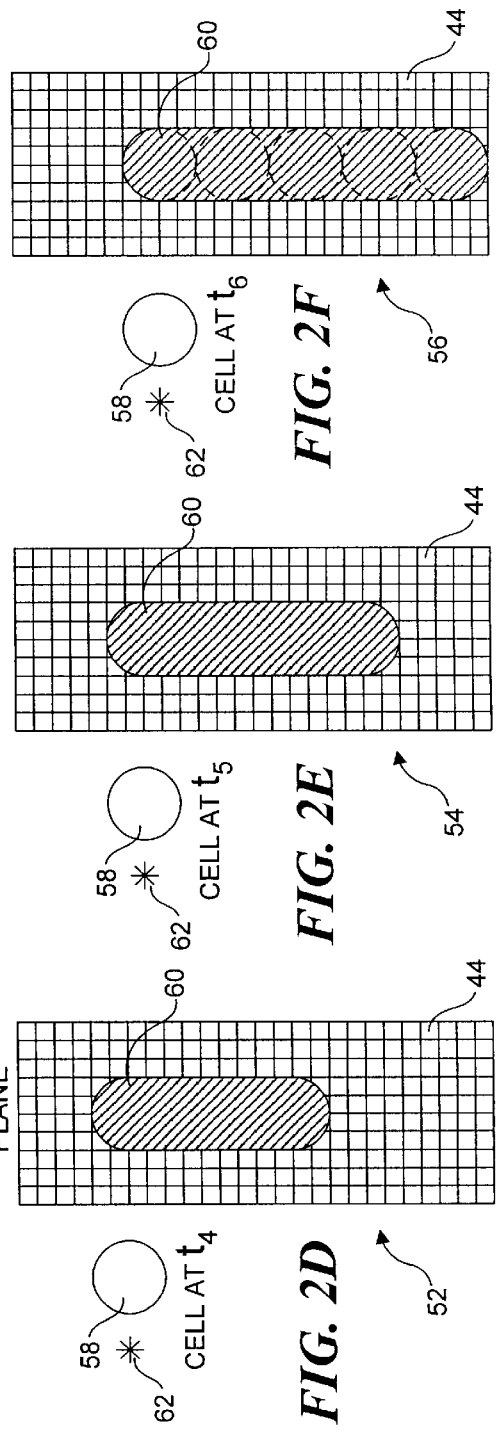

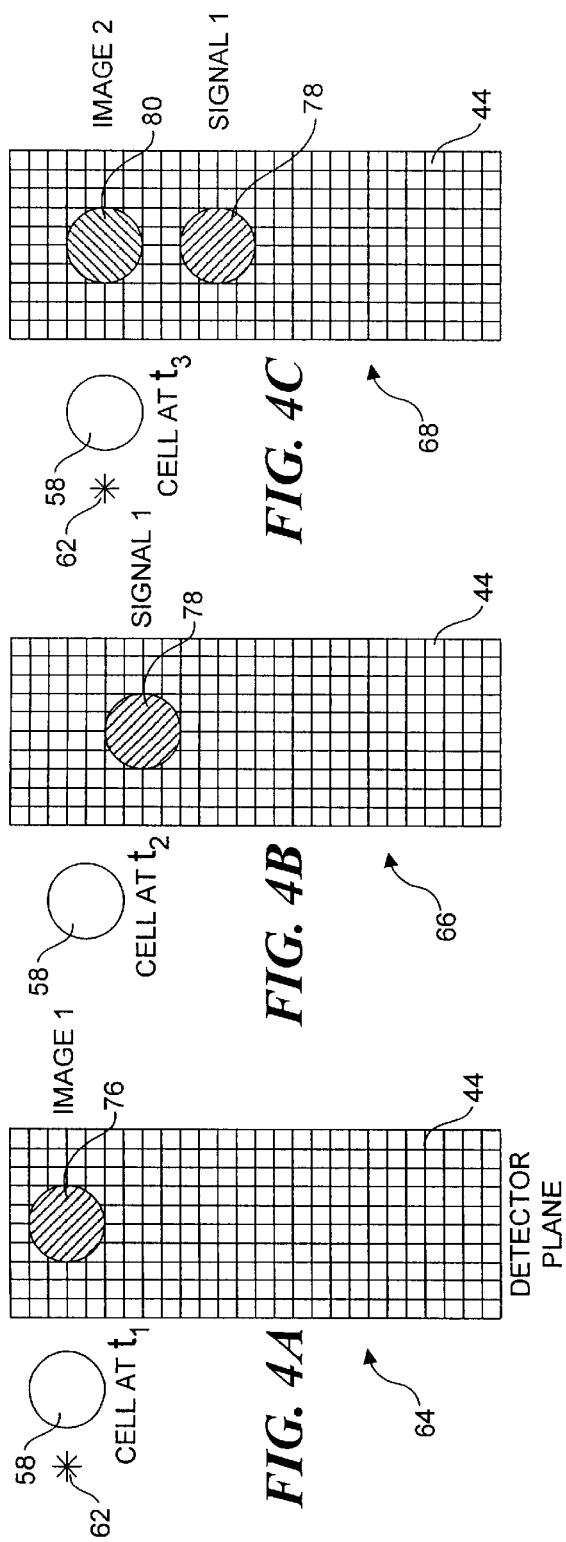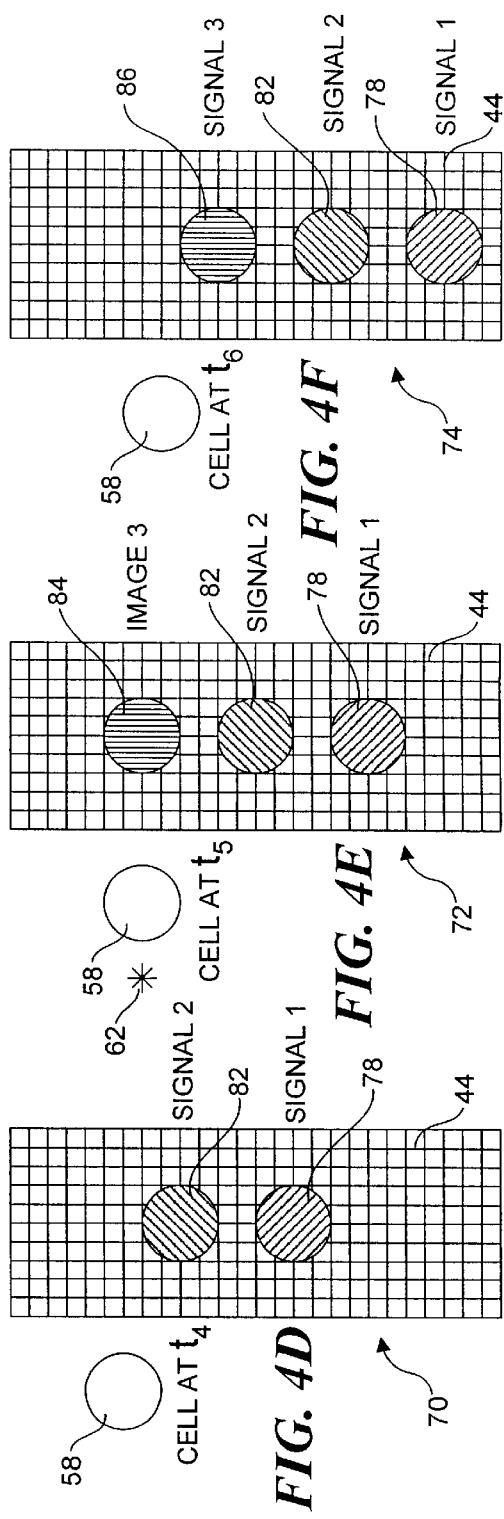

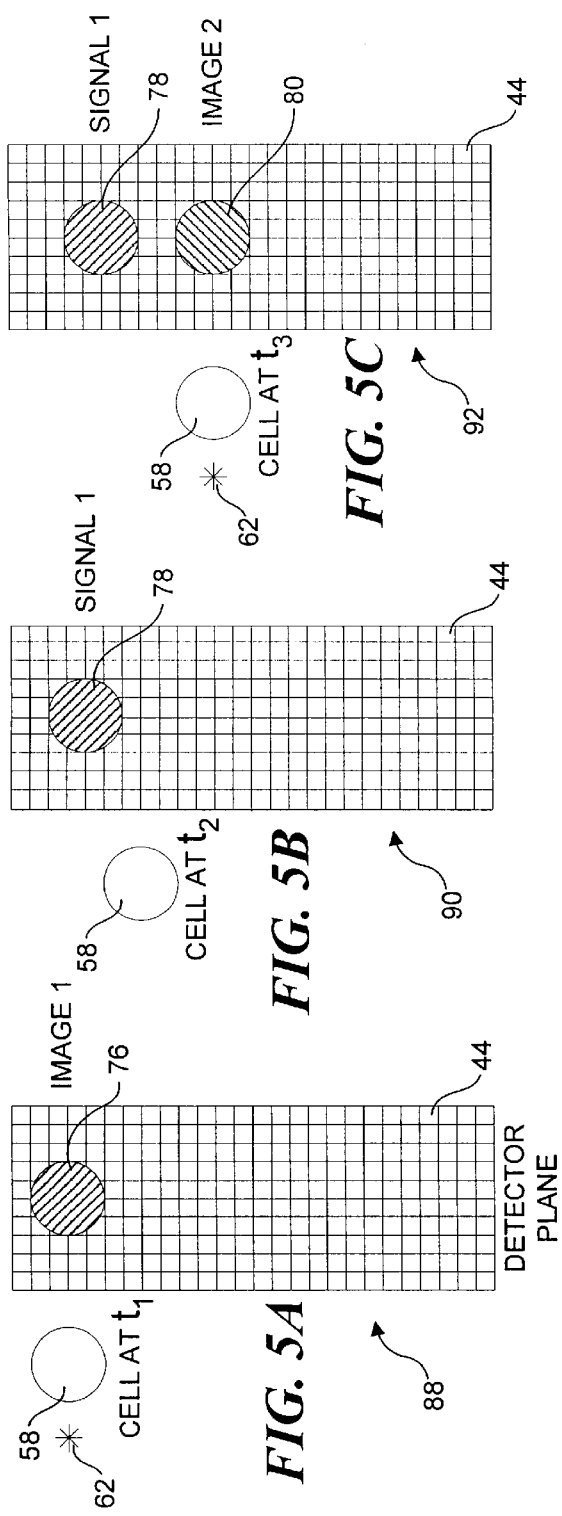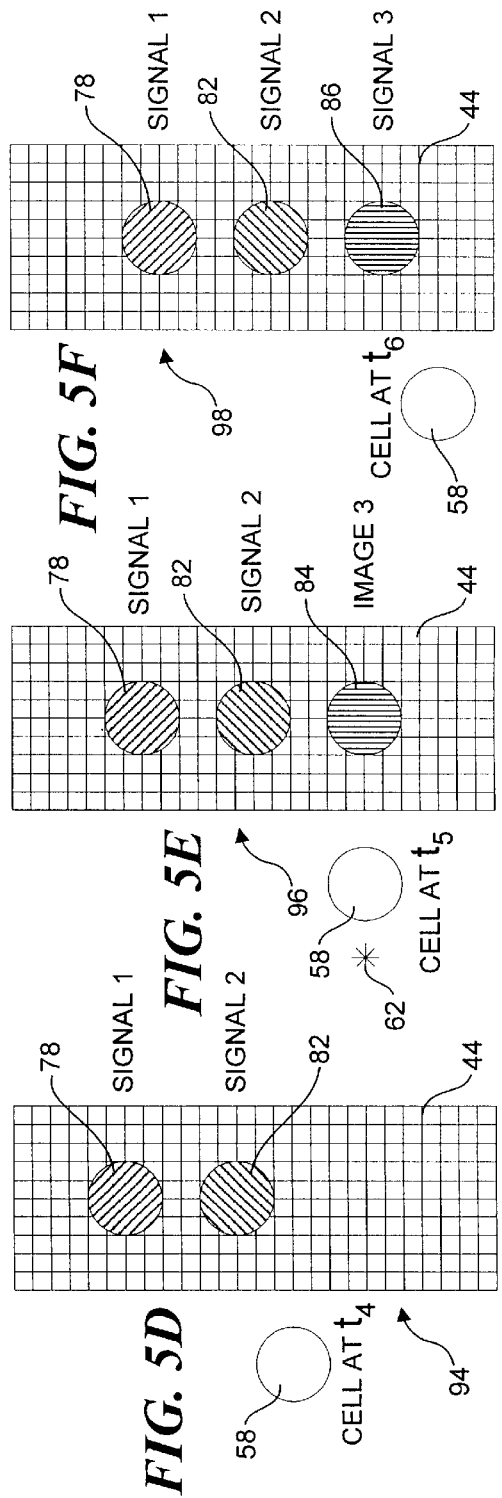

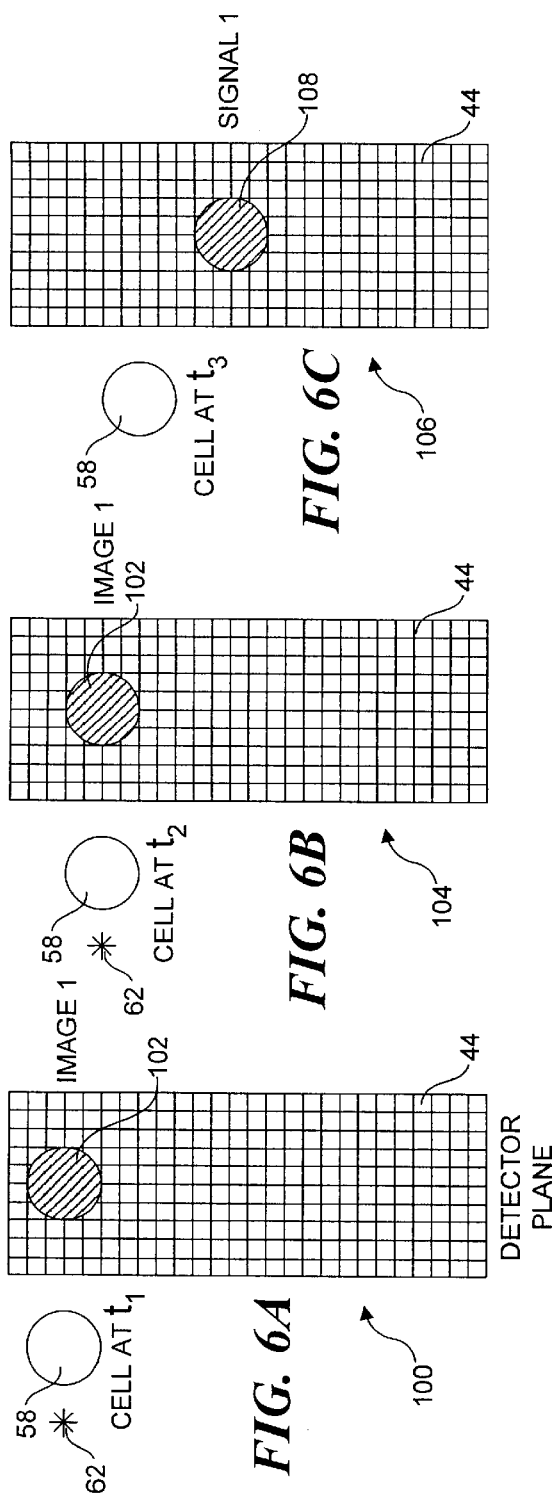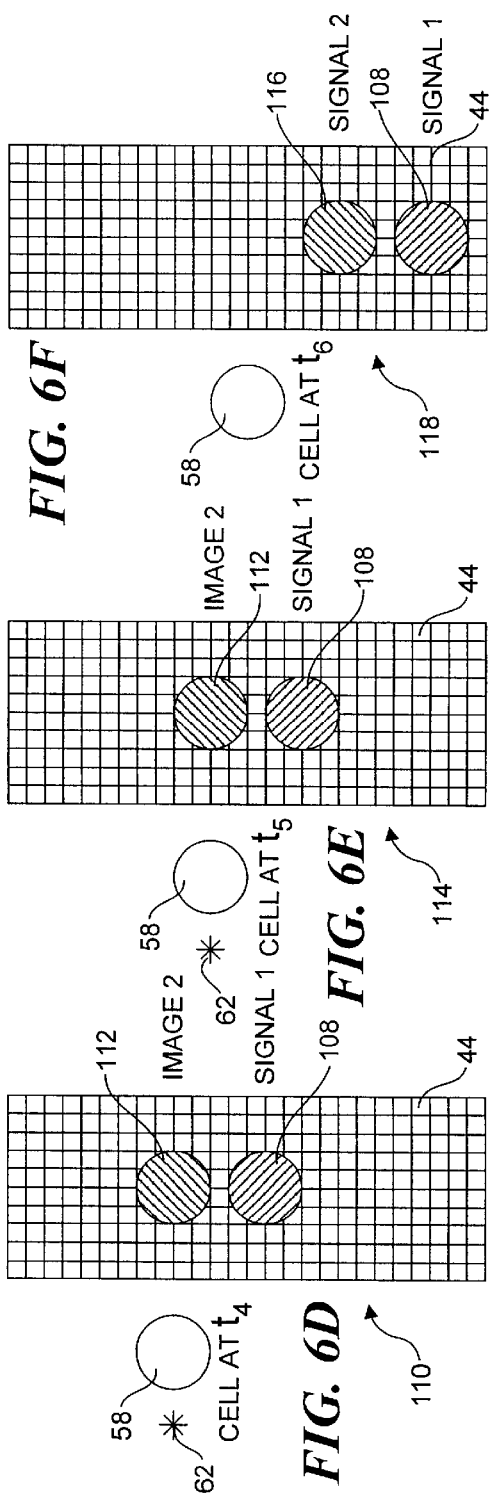

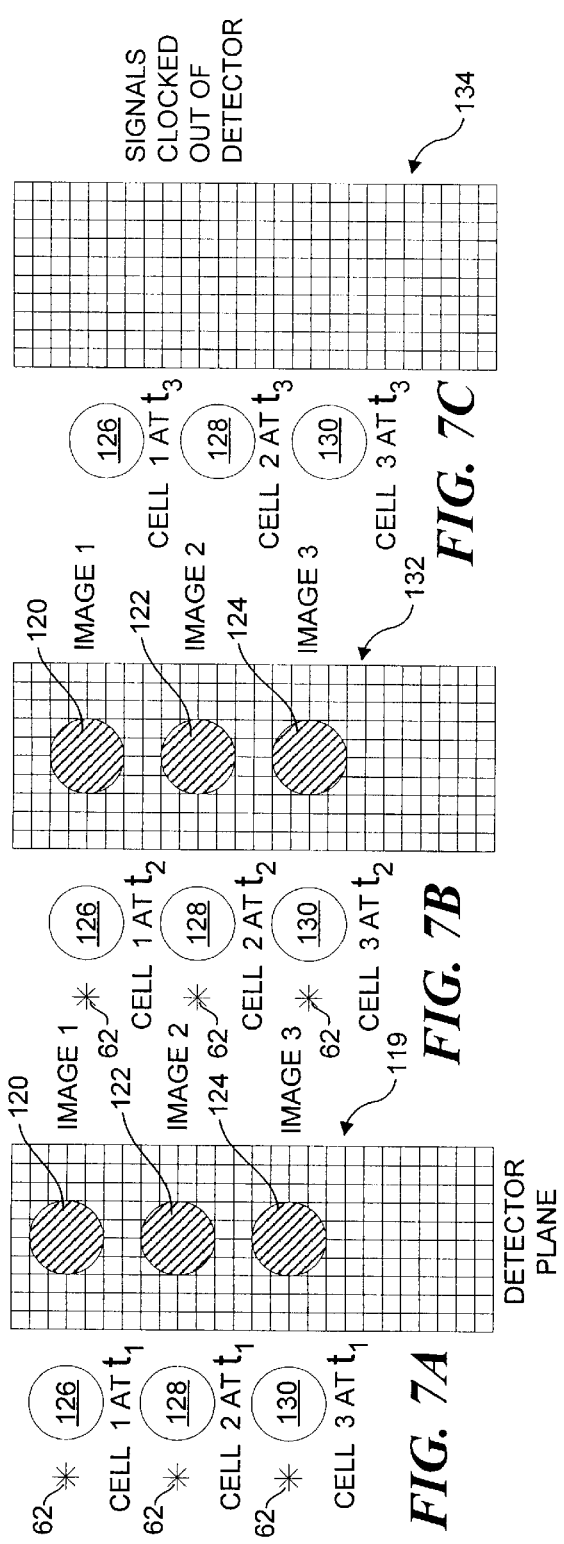
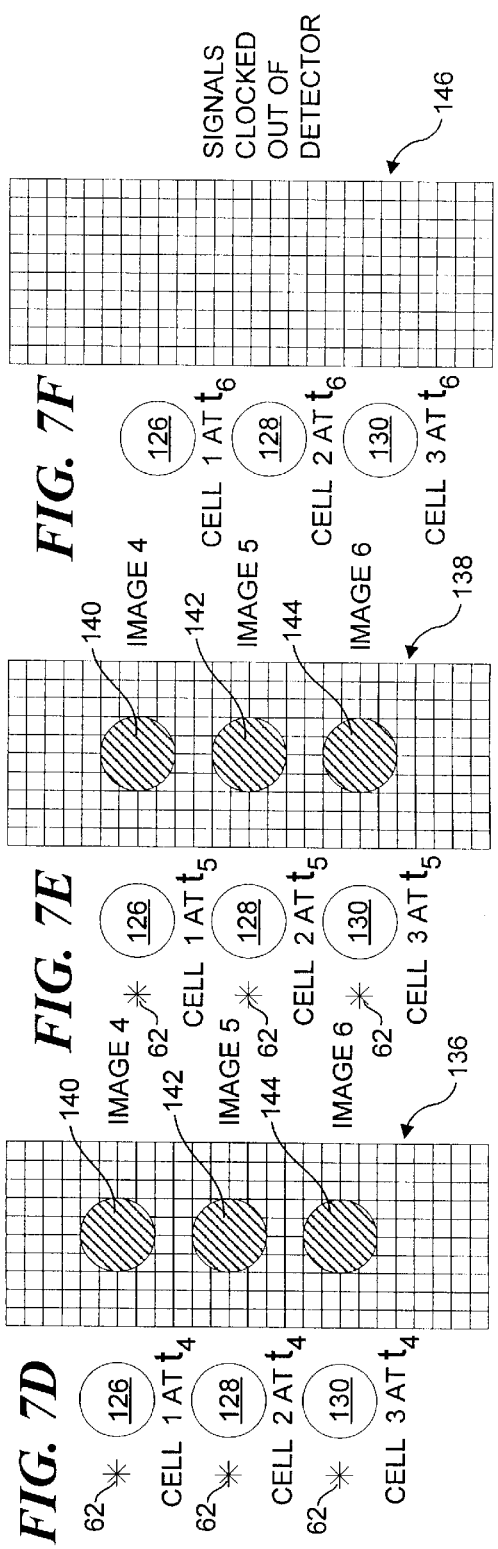

TDI IMAGING SYSTEM FOR KINETIC STUDIES

RELATED APPLICATIONS

This application is based on prior copending provisional patent application Serial No. 60/228,079, filed on Aug. 25, 2000, the benefit of the filing date of which is hereby claimed under 35 U.S.C. §119(e).

FIELD OF THE INVENTION

This invention generally relates to imaging objects or particles for purposes of detection and analysis, and more specifically, to a system and method for analyzing the spectral composition, spatial characteristics, and temporal behavior of objects, such as cells, which may be in motion.

BACKGROUND OF THE INVENTION

Development of new drugs to treat diseases and other medical problems is an expensive and time-consuming process. The efficiency of the drug discovery process is hindered by the limitations of current cell and particle analysis technology. These limitations affect drug discovery at every stage, including: target discovery, target validation, screening, lead optimization, and clinical development. Cell and particle analysis technology is an important aspect of this problem, because one of the goals of the drug discovery process is to understand the biological effect of potential drug compounds on targeted cell types and the collateral effects on other cell types.

In many cases, fluorescent tags are used to label both potential drug compounds and various cellular components in order to detect and analyze binding interactions in both in vitro and in vivo assays. In order to distinguish different compounds and biological targets, each can be labeled with a different fluorescent tag. Therefore, the number of compounds and targets that can be simultaneously studied is limited by the number of colors that can be discriminated. Binding interactions in biological systems are dynamic processes that require evaluation at different points in time. Such interactions can occur over intervals of only a few microseconds. Hence, the ability to discriminate the time sequence of events in an assay is a function of the speed with which repeated fluorescent measurements can be made.

The interactions between compounds and biological targets are preferably studied in an intact cell, in order to detect both beneficial and adverse effects. These effects are often evidenced by the presence or absence of fluorescence in different locations within or around the cell or by changes in cell morphology. Accordingly, the ability to detect the biological activity of a drug candidate is also a function of the spatial resolution of the detection system. Therefore, an ideal system for drug discovery should possess high spectral, temporal, and spatial resolution. An ideal system should further possess high sensitivity to detect low concentrations of biological targets and faint fluorescent signals. Finally, an ideal system would have high throughput to allow the rapid analysis of large compound libraries and numerous biological targets within different cell types.

Rudimentary time-series images of stationary cells can be acquired with a limited set of three or four colors using existing frame-based imaging technology. The measurement frequency of most video imaging systems is approximately 30 Hz, which limits their ability to measure transients that occur in less than about 100 ms. In some cases, the cells under study may be moving, as in microfluidic "lab on chip" systems. In order to prevent image blurring when the cell or objects under study are in motion, the exposure time must be kept very short, which reduces sensitivity.

Accordingly, it will be apparent that an improved technique is desired that resolves the limitations in analyzing the spectra, images, and kinetics of both stationary and moving cells imposed by conventional imaging systems. In addition, a new approach developed to address these problems in the prior art should also have application to the analysis of other types of objects besides cells and should be capable of implementation in different configurations to meet the specific requirements of disparate applications of this technology.

SUMMARY OF THE INVENTION

The present invention is directed to an imaging system that is adapted to determine one or more characteristics of an object from an image of the object. There can be relative movement between the object and the imaging system, and although it is contemplated that either (or both) may be in motion, the object will preferably move while the imaging system is fixed in position. In addition, it should also be understood that while much of the discussion and the claims that follow recite "an object," it is likely that the present invention will preferably be used with a plurality of objects and is particularly useful in connection with a stream of objects or objects moving within a substrate; e.g., in narrow capillaries. Also, it should be understood that as used herein and in the following claims, the terms "image" and "imaging" are broadly applied and are intended to generally refer to the light from an object or objects that is directed onto a surface of a detector; thus, these terms are intended to encompass light from an object or objects that is diffused, dispersed, or blurred on the surface of a detector, as well as light from an object or objects that is focussed onto the surface of the detector, and light from an object or objects that is divided into one or more spectral components incident on the surface of the detector.

The present invention is directed to a method and apparatus for the spectral, spatial, and temporal analysis of cells for purposes of drug discovery and other applications. To achieve such functionality, the present invention rapidly collects image data from moving cells over time. These data can include simultaneous spatial and spectral images covering a wide bandwidth at high resolution. Further, the present invention preserves the spatial origin of the spectral information gathered from the object(s).

In addition, the present invention offers considerable advantages over prior art systems employed for cell and particle analysis. Some of these advantages arise from the novel application of a time delay integration (TDI) detector that produces an output signal in response to the images of cells and other objects that are directed on the TDI detector. The TDI detector that is used in the various embodiments of the present invention preferably comprises a rectangular charge-coupled device (CCD) that employs various specialized pixel read out algorithms, as explained below.

Standard, non-TDI CCD arrays are commonly used for imaging in cameras. In a standard CCD array, photons that are incident on a pixel produce charges that are trapped in the pixel. After image acquisition, the photon charges from each pixel are read out of the detector array by shifting the charges into an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In a TDI detector comprising a CCD array of physical pixels, the CCD array remains exposed to the light as the pixels are read out. The projection of an image on the array of physical pixels generates a pixelated signal. Readout of this signal occurs one row at a time, e.g., from the top to the bottom of the array. Once a first row is read out, the signal pixels in the remaining rows are shifted by one physical pixel in the direction of the row that has just been read. If the object being imaged onto the array moves in synchrony with the motion of the signal pixels, light from the object is integrated without image blurring for the duration of the TDI detector's total readout period. The signal strength produced by a TDI detector increases linearly with the integration period, which is proportional to the number of physical TDI pixel rows, but the noise increases only as the square root of the integration period, resulting in an overall increase in the signal-to-noise ratio by a factor equal to the square root of the number of rows.

If the image of the object moves synchronously with the pixelated signal (in the same direction and with the same speed), light forming each portion of the image is detected in the same portion of the pixelated signal over time, regardless of the motion. Conversely, if the image of the object moves asynchronously relative to the pixelated signal, (at a different speed and/or in a different direction), light forming each portion of the image at later times will not be detected in the same portion of the pixelated signal that corresponded to the image portion at an earlier time. By intentionally desynchronizing the motion of the pixelated signal on the TDI detector from the motion of the image, temporally distinct pixelated signals are produced. The desynchronization can result from a difference in the speed of the image relative to the signal and/or a difference in the direction of motion between the two. In this manner, time-resolved measurements of morphology and spectral emission characteristics are performed.

In the present invention, there are four entities that may be in motion. These include the object being imaged, the image of the object projected on the detector, the detector itself, and the signal generated by the image on the detector. Any movement of the object relative to the detector results in movement of the image across the detector. However, movement of the object is not required in the present invention. Depending on the embodiment of the invention, there may or may not be relative motion between the image and the detector. TDI imaging, unlike other imaging methods, involves the movement of the signal across the detector while the measurement is being performed. However, the signal need not move in synchrony with the image of the object. In the present invention, the velocity of signal motion is a controllable parameter that can be adjusted in order to measure various features of the object being imaged. The signal can be made to move faster, slower, or in a different direction than the image, which may or may not itself be moving. Further, the movement of the signal can be changed dynamically during the measurement. The nature of the asynchrony in part determines the features of an object or objects that can be measured.

In several embodiments of the present invention, relative movement will exist between the object being imaged and the imaging system, and in most cases, it will be more convenient to move the object than to move the imaging system. However, it is also contemplated that in some cases, the object may remain stationary, and the imaging system move relative to it. As a further alternative, both the imaging system and the object may be in motion, but in different directions or at different rates. Regardless of whether there is relative movement between the object and the imaging system, there will be a movement of the signal across the detector. The synchrony of signal movement is preferably adjusted by changing either the speed of the object, the speed of the signal, or the direction of the signal.

Another adjustable parameter in the present invention is the continuity of signal generation. In some embodiments of the invention, the signal from the object is detected continuously. An exemplary application of continuous detection would be the imaging of a cell containing a chemiluminescent substrate that constantly emits light. Another example is a cell illuminated by a continuous-wave laser or arc lamp, forming either a scatter, absorption, or fluorescence image on the detector. In other embodiments of the present invention, the signal from the object is detected in a discontinuous fashion. For example, a discontinuous detection occurs if a cell is illuminated by a pulsed or modulated laser, forming either transient scatter, absorption, or fluorescence images on the detector. Another example of discontinuous detection occurs if a chemiluminescent cell is imaged via a shuttered or gated TDI detector. Signal continuity, when controlled in combination with the synchrony of signal readout, gives rise to various modes of operation of the present invention.

BRIEF DESCRIPTION OF THE DRAWINGS FIGURES

The foregoing aspects and many of the attendant advantages of this invention will become more readily appreciated as the same becomes better understood by reference to the following detailed description, when taken in conjunction with the accompanying drawings, wherein:

FIGS. 1A, 1B, and 1C are respectively a plan view, an elevational view, and an isometric view of an exemplary imaging system suitable for implementing the present invention, in which particles conveyed by a fluid stream are imaged on a TDI detector;

FIGS. 2A–2F are a plurality of images of an object produced on the TDI detector over time, for a first embodiment of the present invention in which an object is detected continuously, and the signals produced by the TDI detector in response to the images of the object are rapidly clocked;

FIGS. 4A–4F are a plurality of images of an object over time, illustrating the operation of a second embodiment of the present invention in which an object is detected discontinuously, and the TDI detector signals are rapidly clocked;

FIGS. 5A–5F are a plurality of images of an object over time, illustrating the operation of the second embodiment of the present invention in which an object is detected discontinuously, and the TDI detector signals are slowly clocked;

Figure 1A:
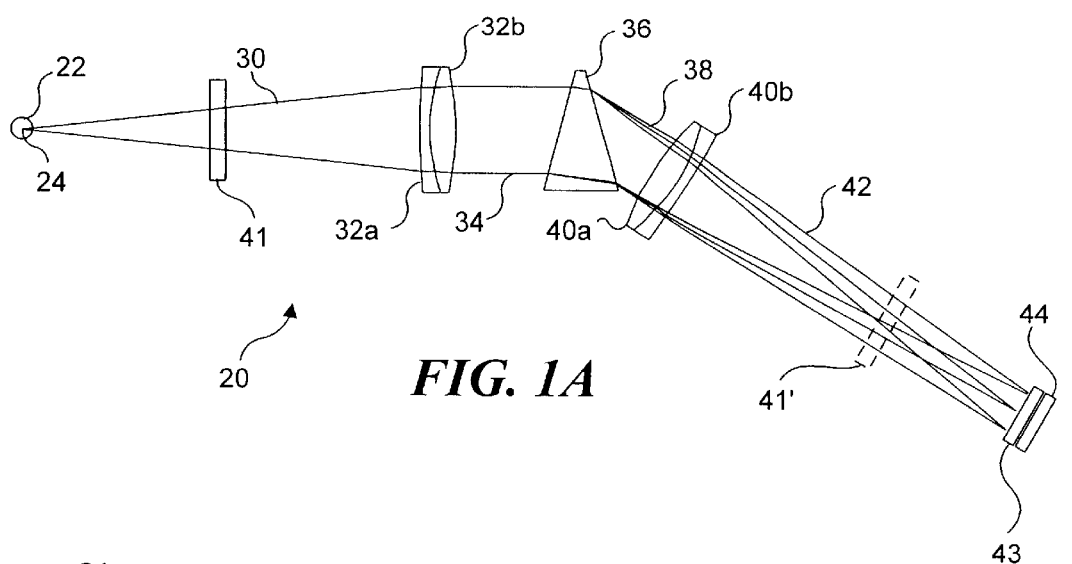

FIGS. 6A–6F are a time series illustrating the operation of a third embodiment of the invention in which an object is detected discontinuously, and the detector signals are alternately clocked synchronously and then rapidly clocked; and FIGS. 7A–7F comprise a time series illustrating the operation of a fourth embodiment of the present invention in which a plurality of objects are detected discontinuously, and the signals produced by the detector in response to the images of the objects are alternately clocked synchronously and then rapidly clocked completely off the detector.

DESCRIPTION OF THE PREFERRED EMBODIMENT

The present invention offers considerable advantages over systems employed for cell and particle analysis in the prior art. In some embodiments of the present invention, these advantages arise from the use of an optical dispersion system in combination with a TDI detector to produce an output signal in response to the images of cells and other objects that are directed onto the TDI detector. Multiple objects can be imaged on the TDI detector at the same time. In addition, the image of each object can be spectrally decomposed to discriminate object features by absorption, scatter, reflection, or probe emissions, using a common TDI detector for the analysis.

The present invention can be employed to determine morphological, photometric and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can be stimulated into either fluorescence or phosphorescence to emit light, or may be luminescent, producing light without stimulation. In each case, the light from the object is imaged on the TDI detector of the present invention, and the output signal of the detector is analyzed to determine the presence and amplitude of the emitted light, the number of discrete positions in a cell or other object from which the light signal(s) originate(s), the relative position of the signal sources, and the color (wavelength or waveband) of the light emitted at each position in the object.

An initial application of the imaging system comprising the present invention will likely be as a cell analyzer to determine one or more of the parameters listed above, for cells entrained in a fluid flowing through the imaging system. However, it should also be understood that this invention can be used for imaging other types of moving objects.

The present invention concerns alternative detector configurations and modes of operation in connection with various imaging system embodiments disclosed in the commonly assigned copending U.S. patent applications noted above, including Ser. Nos. 09/490,478 and 09/538,604, the complete disclosure, specification, and drawings of which are hereby specifically incorporated herein by reference. For convenience, portions of the first of these application are reproduced below in order to facilitate access to portions of its disclosure that will enable a better understanding of how the various embodiments of the present invention are implemented. However, it will be understood that the present invention can be implemented with other imaging system configurations disclosed in the above-identified applications, which are not specifically discussed herein, as well as with other imaging systems of similar configurations.

Suitable Imaging System

Figure 1B:
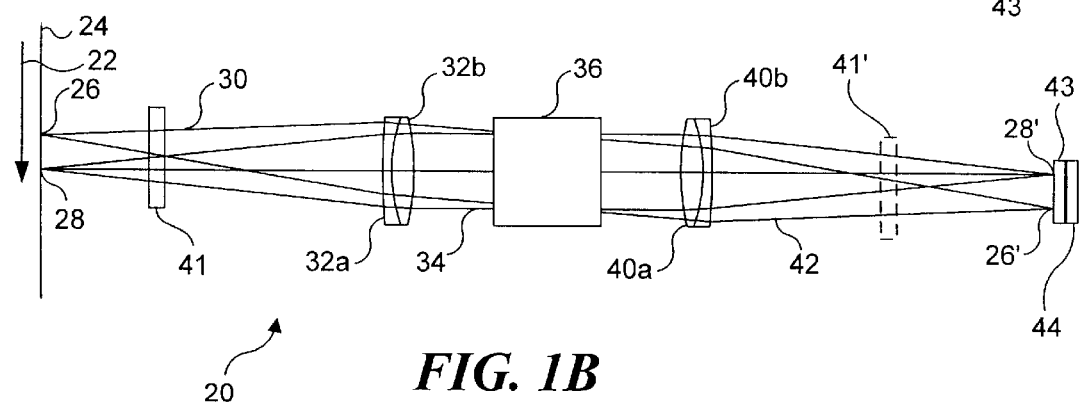
Figure 1C:
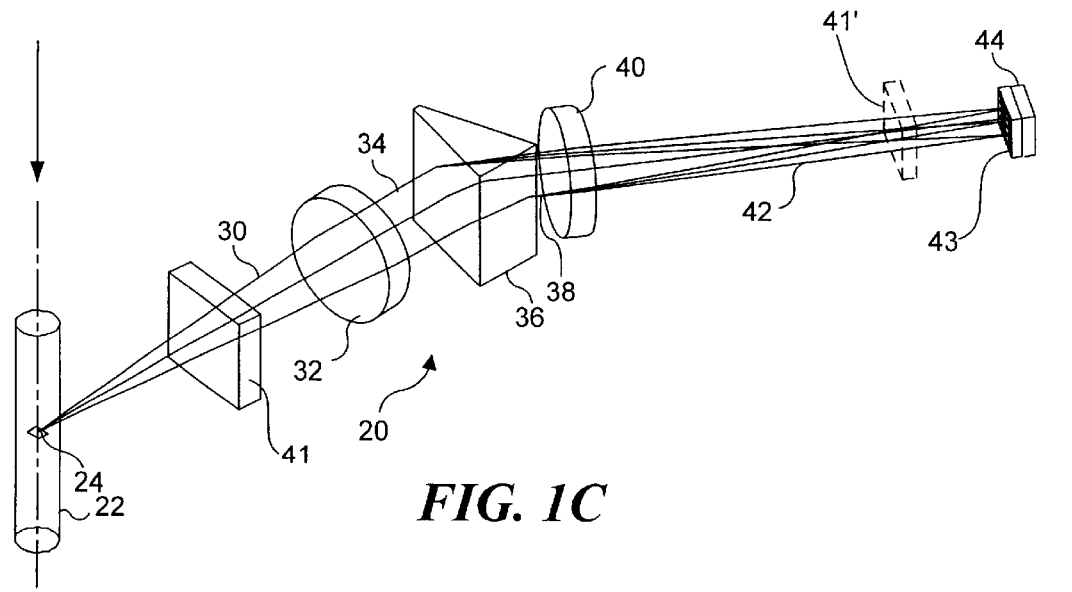

A first exemplary configuration of an imaging system 20 that is suitable for implementation of the present invention as described below is schematically illustrated in FIGS. 1A–1C, for use in producing images of moving objects such as cells that are conveyed by a fluid flow 22 through the imaging system. In FIG. 1A, fluid flow 22 entrains an object 24 (such as a cell, but alternatively, a different type of small particle) and carries the object through the imaging system. The direction of the fluid flow in FIG. 1A is into (or out of) the sheet, while in FIGS. 1B–1C, the direction of fluid flow is from top to bottom, as indicated by the arrow to the left of the figures. Light 30 from object 24 passes through collection lenses 32a and 32b that collect the light, producing collected light 34, which is approximately focussed at infinity, i.e., the rays of collected light are generally parallel. Collected light 34 enters an optional dispersing element 36, which disperses the light, producing dispersed light 38. The dispersed light then enters imaging lenses 40a and 40b, which focus light 42 onto a TDI detector 44. (It should be noted that as used throughout this specification and in the claims that follow, a TDI detector can generally be oriented in different positions, so that the terms "row" and "column," "up" and "down," and "left" and "right" as applied to a TDI detector are meaningful in regard to each exemplary illustration, but are not intended to be limiting in regard to the scope of the claims.)

In the embodiment shown in FIGS. 1A–1C, imaging system 20 may optionally include dispersing element 36 to spectrally disperse light onto the TDI detector. The use of a dispersing element enables the present invention to independently analyze the kinetics of multiple colors simultaneously. Also as shown in FIGS. 1A–1C, imaging system 20 may optionally include a shutter 41 or a gated image intensifier 43. In these instances, shutter 41 or gated image intensifier 43 are used to interrupt the signal collection, so as to produce a discontinuous image that is incident upon TDI detector 44. In general, shutter 41 can be disposed anywhere along the light path, including between object 24 and collection lenses 32a and 32b, or between imaging lenses 40a and 40b and TDI detector 44, as indicated by the illustrated disposition of a shutter 41'. Gated image intensifier 43 is preferably located at an intermediate image plane or in close proximity to TDI detector 44. If the embodiment includes a spectral dispersing element, then gated image intensifier 43 is disposed after the dispersing element, at an intermediate image plane ("after" being relative to the direction of light transmission through the imaging system), or on TDI detector 44. Further details of the use of shutter 41 and gated image intensifier 43 are discussed below.

With reference to FIG. 1B, if it is assumed that the Figure depicts the imaging of object 24 over time, the object is shown at both a position 26 and a position 28 as it moves with fluid flow 22. As a consequence, images of object 24 will be produced on the detector at two discrete spatial positions 26' and 28', as indicated on the right side of FIG. 1B. Alternatively, if it is assumed that FIG. 1B is depicting a single instant in time, positions 26 and 28 represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32a and 32b. Lens elements of different designs, either simpler or more complex, can alternatively be used in constructing the imaging system to provide the desired optical performance, as will be understood by those of ordinary skill in the art. The simplicity or complexity of the actual lenses or optical elements used in the imaging system will depend upon the particular type of imaging application for which the imaging system will be employed. It is further noted that imaging systems not including a light-dispersing element 36 (such as the prism illustrated in this example), may also be implemented to provide the present invention.

Furthermore, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion, but either in different directions or at different rates.

The TDI detector that is used in the various embodiments of the present invention preferably comprises a rectangular charge-coupled device (CCD) that employs a specialized pixel readout algorithm, as explained below. Non-TDI CCD arrays are commonly used for two-dimensional imaging in cameras. In a standard CCD array, photons that are incident on a pixel position produce charges that are trapped in the pixel position. The photon charges from each pixel position are readout of the detector array by shifting the charges from one pixel to the next, and then transferring the charges to an output capacitor, producing a voltage proportional to the charge. Between pixel readings, the capacitor is discharged and the process is repeated for successive pixels on the chip. During the readout, the array must be shielded from any light exposure to prevent charge generation in the pixels that have not yet been read.

In one type of TDI detector 44, which preferably comprises a CCD array, the CCD array remains exposed to the light as the pixels are read out. The readout occurs one row at a time from the top toward the bottom of the array. Once a first row is read out, the remaining rows are shifted by one pixel in the direction of (i.e., toward) the row that has just been read. If the object being imaged onto the array moves in synchrony with the motion of the pixels, light from the object is integrated for the duration of the TDI detector's total readout period without image blurring. The signal strength produced by a TDI detector increases linearly with the integration period, which is proportional to the number of TDI rows, but the noise increases only as the square root of the integration period, resulting in an overall increase in the signal-to-noise ratio over a conventional CCD array by a factor equal to the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have a different configuration of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other exemplary imaging systems described herein that employ a fluid flow to carry objects through the imaging system, a flow-through cuvette or a jet (not shown) contains the cells or other objects being analyzed. The velocity and cellular concentration of the fluid may be controlled using syringe pumps, gas pressure, or other pumping apparatus (not shown) or methods to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed. The number of regions will also depend on the actual size of the object being imaged and its distance from the imaging system. It is envisioned that the present invention has applications to technology ranging from the analysis of cells and other microscopic objects to the imaging of stellar objects.

It should be emphasized that the present invention is not limited to CCD types of TDI detectors. Other types of TDI detectors, such as electron bombardment CCDs, complementary metal oxide semiconductors (CMOS), and multi-channel plate imaging devices might alternatively be used for the TDI detector in the present invention. It is important to understand that any pixelated device (i.e., a device having a multitude of light sensitive regions) in which a signal produced in response to radiation directed at the device can be caused to move through the device in a controlled fashion is suitable for use as the TDI detector in the present invention. Typically, during operation of a TDI detector, the signal moves in synchrony with a moving image projected onto the device, thereby increasing the integration time for the image without causing blurring. However, it is very important to understand that in the present invention, the motion of the signal is selectively desynchronized from the motion of the image, and the desynchronization is controlled as required to achieve a desired effect.

First Preferred Embodiment

In accord with a first preferred embodiment, a signal readout from TDI detector 44 is asynchronous, such that the velocity of the pixelated signal differs from the velocity of the image on the TDI detector by a fixed amount for the entire time that the image of the object is projected onto the TDI detector. If the velocity of the image across the TDI detector is $V_i$, the velocity of the detector signal is $V_s$, and the pixel height is P, the time, $T_p$, it takes for the image and the pixelated signal to diverge by one row of pixels is defined by:

$$T_p = |P/(V_s - V_i)|. \qquad (1)$$

Note that the velocities can be in opposite directions, and either velocity can be zero in this and the other preferred embodiments of the invention described below.

FIGS. 2A–2F show a plurality of time frames 46, 48, 50, 52, 54, and 56 corresponding to a time series that illustrates the operation of one preferred embodiment of the present invention. In first time frame 46, an image of a cell 58 is projected onto TDI detector 44, which produces a signal 60. The image is created either directly, with illumination 62 directed along the optic axis of the imaging system (e.g., along the optic axis of imaging system 20) or indirectly, such as by scatter of light by the object, or as a result of fluorescence emitted from the object, with illumination directed at an angle relative to the optic axis. Note that the cell is moving downwardly relative to the TDI detector, as indicated by the arrow labeled "cell movement" in FIG. 2A. In each successive time frame of this example, the cell has moved one pixel row lower than in the previous time frame, and the top of the image of the cell on the TDI detector has also moved one pixel row down from that in the previous frame. The time series of FIGS. 2A–2F illustrates the case when the illumination is continuous, as indicated by the presence of illumination 62 in all time frames of the time series. Signal 60 is clocked from the TDI detector at a rate that is four times faster than the movement of the image of the cell relative to TDI detector 44, causing the image and corresponding signal to increasingly elongate on the detector in successive time frames 48, 50, 52, 54, and 56. Once the portion of signal 60 in time frame 46 corresponding to one cell height passes the bottom of cell 58, which occurs between time frames 48 and 50, the portion of the signal that has propagated beyond the image of the cell is no longer influenced by light from the cell and constitutes an independent measurement from the preceding time period. Hence, by sixth time frame 56, signal 60 can be segmented into five independent measurements of cell 58 at different times on the basis of the height of the signal and the height of the cell. These five independent measurements are illustrated in sixth time frame 56 of FIG. 2F by dash line circles.

If the magnification of the system is such that the image is only one pixel high, each row of pixels read from TDI detector 44 will comprise an independent measurement of the object with a time resolution of $T_p$. The value of $T_p$ is typically less than 30 μs for commercial TDI detectors imaging slowly moving objects. Compared to a standard video camera running at 30 frames per second, as is employed in the prior art, the present invention offers up to three orders of magnitude better time resolution between independent measurements.

If the image of the object vertically spans N rows of pixels, the time resolution will be lower and is given by the product, $N*T_p$. Because of the continuity of signal detection in this embodiment, as the signal and image diverge on the TDI detector, an image spanning N pixels will be blurred in the axis of relative motion between the signal and the image. In contrast, blurring will not occur in the lateral image axis.

Figure 3:
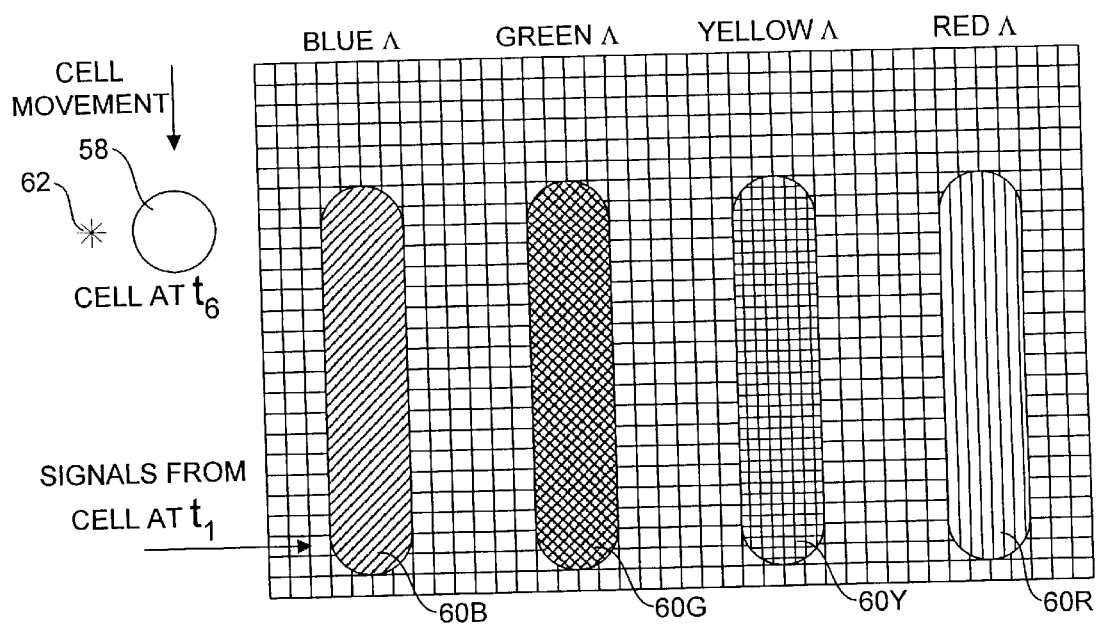
FIG. 3 illustrates a spectral separation of images on the TDI detector when the first embodiment of the present invention operates with continuous detection and a spectral dispersing collection system.

When the present invention incorporates a lateral spectral dispersion system such as that shown in FIGS. 1A–1C, spectral information will be preserved regardless of image size. In this manner, the present invention can be employed to monitor fluorescence spectral kinetics and other time-variant signal parameters from a cell on a substrate or in a fluid stream. FIG. 3 illustrates the image seen on TDI detector 44 at time $t_6$, for the case when the imaging system employs spectral dispersing element 36, such as the prism as shown in FIGS. 1A–1C. The spectral dispersing element spreads different colors of the light from the object across the TDI detector such that different regions on the detector receive light corresponding to different light wavelengths. With respect to FIG. 3, these wavelength regions include a blue wavelength region that produces a signal 60B, a green wavelength region that produces a signal 60G, a yellow wavelength region that produces a signal 60Y, and a red wavelength region that produces a signal 60R.

It will also be apparent that a dispersing system can be employed in any embodiments of the present invention. Furthermore, the dispersion can be performed on the basis of polarization, phase, wavelength, or other optical parameters.

Second Preferred Embodiment

A second preferred embodiment minimizes image blur. This embodiment uses a readout mode similar to that of the first embodiment in that the signal readout from the TDI detector is asynchronous, such that the velocity of the pixelated signal differs from the velocity of the image by a fixed amount. However, unlike the first preferred embodiment, in the second preferred embodiment, the illumination is intermittent. Alternatively, if the object is subject to continuous illumination or is self-luminescent, the signal collection process in this embodiment is made to be discontinuous. Intermittent illumination can be effected with a pulsed laser or other type of pulsed or strobed light source. If the object being imaged is self-luminescent or is illuminated continuously, shutter 41 or gated image intensifier 43 can be employed between the object and the detector to produce discontinuous detection, as described above with reference to the imaging system shown in FIGS. 1A, 1B, and 1C.

In this second preferred embodiment, discontinuous detection is used to increase image acquisition throughput and to prevent image blurring, despite the difference between signal and image velocities produced by asynchronous readout of the TDI detector. Image integrity is preserved by limiting the object's detection time to less than $T_p$, the time it takes for the image and the signal to diverge on the TDI detector by one pixel. Preferably, control of the detection period is achieved by controlling the duration of illumination reaching the TDI detector. In the case of continuously illuminated or self-luminescent objects, shutter 41 or gated image intensifier 43 is controlled mechanically or electronically such that the TDI detector is exposed to light from the object during each detection period for a time less than $T_p$. After a detection period, the subsequent detection period is delayed until the image and the signal have diverged on the detector by a distance equal to or greater than the image height. In this manner, multiple unblurred images of an object can be detected in rapid succession. In comparison to a frame-mode detector, which must be completely read out after each detection period, the second embodiment of the present invention can produce substantially higher image acquisition rates by a factor approximately equal to the ratio of the TDI detector height to the image height on the TDI detector.

FIGS. 4A–4F illustrate a plurality of time frames corresponding to a time-series of a first operating mode in accord with the second preferred embodiment. This operating mode is similar to that illustrated for the first preferred embodiment, with the exception that illumination is discontinuous. In a first time frame 64, illumination 62 of cell 58 is limited to less than the time it takes a first image 76 to travel one pixel on TDI detector 44, halting before a second time frame 66. In second time frame 66, a first signal 78 generated by the first image is clocked down TDI detector 44 at a ratio of four pixels on the detector for each pixel of image movement. In a third time frame 68, first signal 78 has diverged from the position of cell 58 on TDI detector 44, and illumination 62 is restored briefly to generate a second image 80. Illumination is again halted by a fourth frame 70, while first signal 78 and a second signal 82 produced in response to second image 80 propagate down the detector until the divergence has again exceeded the image height. This process continues, generating successive image signals at different times for a cell that is in view, as shown, for example, by a third image 84 and a third signal 86 in FIGS. 4E and 4F, corresponding to fifth and sixth time frames 72 and 74.

With reference to FIGS. 5A–5F, a plurality of time frames 88, 90, 92, 94, 96, and 98 produced in accord with another operating mode of the second embodiment are shown. In this mode, the velocity of cell 58 is higher than the clock rate of the signals from TDI detector 44, in contrast to FIGS. 4A–4F, wherein the clock rate of the signals is higher than the velocity of the cell. Since the cell is moving faster than the signal is being clocked from the TDI detector, successive images 76, 80, and 84, and corresponding successive signals 78, 82, and 86 are produced and the cell is below each successive signal. Otherwise, the results from this mode of operation for the second embodiment are essentially identical to those for the mode described above, with reference to FIGS. 4A–4F.

Third Preferred Embodiment

In the third preferred embodiment, the difference in velocity between the image and the signal is not fixed. Instead of fixed asynchronous operation, the signal and image velocity remain synchronized for a first period of time, followed by a second period of asynchrony. During the synchronous period, the signal is integrated without blurring. During the subsequent asynchronous period, the signal velocity is changed to cause a divergence of the signal and image. After the divergence has exceeded the image height, synchronous operation is resumed.

FIGS. 6A–6F illustrate this quasi-synchronous operation of the third embodiment. In a first time frame 100, illumination 62 is applied to cell 58 to produce a first image 102 on TDI detector 44. Illumination 62 continues into a second time frame 104, despite the fact that first image 102 propagates through more than one row of pixels. Image blurring is prevented because first image 102 propagates in synchrony with cell 58. Illumination 62 is halted in a third time frame 106, and a first signal 108 that was generated in response to first image 102 is rapidly clocked down TDI detector 44 through a distance greater than the image height. In a fourth time frame 110, synchronous clocking is resumed, and illumination 62 is re-established, producing a second image 112. Again, second image 112 is integrated through a fifth time frame 114, at which point, the signals are rapidly clocked, producing a second signal 116 during a sixth time frame 118.

The third embodiment approaches the high image acquisition rates of the second embodiment, but because the synchronous periods enable the extended integration of multiple strobe flashes, continuously-illuminated or self-luminescent objects without blurring, the sensitivity of the third embodiment can exceed that of the second embodiment.

In the previous three embodiments, the temporal resolution of kinetic measurements are independent of the speed with which the cell or other object moves over the detector and independent of the number of pixels in the detector array. With a continuous illumination source or self-luminous object, the pixel clock rate down the TDI detector is adjusted to produce a desired time period between kinetic measurements. With a pulsed source, the pixel clock rate and pulse period are adjusted in concert to produce the desired kinetic measurement period. Because the velocity of the signal on a TDI detector is a function of only the number of pixels in a row, and not the total number of pixels on the detector, temporal resolution in the previous embodiments can exceed that of frame imaging systems by several orders of magnitude, enabling the kinetic measurement of biological phenomena that cannot be studied using frame imaging. For example, when a continuous source or self-luminous object is being analyzed, the pixel clock rate may be set to 100 milliseconds for the measurement of morphological changes in cells or changes in protein expression, 10 milliseconds to measure muscle fiber contractions, 100 microseconds for nerve synapse studies, or 1 microsecond for cell depolarization measurements. The present invention enables the kinetic measurements of many objects in parallel, over measurement periods covering many orders of magnitude. In particular, the present invention enables measurements of many objects in parallel, with spectral and spatial resolution over short time intervals previously unachievable with conventional methods.

Fourth Preferred Embodiment

The fourth preferred embodiment is similar to the third embodiment in that it employs quasi-synchronous operation. However, unlike the third embodiment, the asynchronous clocking period is extended so that the entire TDI array is rapidly clocked out between synchronous periods. The clearing of the detector between synchronous periods facilitates the simultaneous imaging of multiple cells along the axis of motion, as illustrated in FIGS. 7A–7F. In a first time frame 119, images 120, 122, and 124 of cells 126, 128, 130 respectively, are projected onto TDI detector 44. As shown in FIGS. 6A–6F, the duration of illumination 62 spans first time frame 119 and a second time frame 132 without image blurring due to synchronous clocking of TDI detector 44. In a third time frame 134, the integrated signals generated by cells 126, 128, and 130 are clocked out of the detector. Synchronous operation commences once again in a fourth time frame 136 and continues through a fifth time frame 138, enabling the detection of a second series of images 140, 142, and 144, which are clocked out of TDI detector 44 in a sixth time frame 146.

In each of the above three embodiments, the signals collected from an object at earlier times diverge increasingly from the position of the image on the detector. If multiple cells along the axis of motion are imaged simultaneously, their signals may eventually overlap on the detector, causing crosstalk. Crosstalk is prevented in the fourth embodiment, albeit at the expense of temporal resolution, because the signals detected for the images of all the cells in view during a single synchronous period are completely clocked out of the TDI detector before another synchronous period commences. However, unlike conventional frame-based imaging systems, sensitivity is increased in this embodiment due to the extended integration period afforded by the transiently synchronous operation of the TDI detector. It will be clear to those of ordinary skill in the art that the step of suspending signal collection after a period of synchronous or asynchronous operation and clearing the array before crosstalk occurs can be applied to any embodiment of the present invention.

Although the present invention has been described in connection with several preferred forms of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for detecting one or more characteristics of an object with a time delay integration (TDI) detector wherein there is a relative movement between an image of the object and the TDI detector, comprising the steps of:
   (a) directing light from the object onto the TDI detector to form an image of the object onto the TDI detector, said TDI detector producing an output signal corresponding to the image, said output signal propagating over the TDI detector with a velocity;
   (b) operating in an asynchronous mode in which a difference in a velocity of the image of the object on the TDI detector and the velocity of the output signal propagating over the TDI detector exists, for at least part of a time during which the output signal is propagating over the TDI detector; and (c) evaluating the output signal of the TDI detector to determine at least one characteristic of the object.

2. The method of claim 1, wherein the image of the object blurs as the output signal of the TDI detector propagates over the TDI detector.

3. The method of claim 1, wherein the step of evaluating the output signal comprises the step of determining at least one of a waveband component, a wavelength component, a phase, and a polarization of the light directed onto the TDI detector from the object.

4. The method of claim 1, wherein the difference in the velocity is fixed.

5. The method of claim 4, further comprising the step of discontinuously detecting light from the object with the TDI detector, so that the output signal propagating over the TDI detector diverges away from the image formed by light of the object on the TDI detector by less than a pixel while the object is being imaged on the TDI detector.

6. The method of claim 5, wherein the step of discontinuously detecting comprises the step of periodically preventing light from the object reaching the TDI detector for a sufficient time to enable the output signal to propagate over the TDI detector from where a subsequent image is formed on the TDI detector by a distance at least equal to a dimension of the image of the object on the TDI detector.

7. The method of claim 5, wherein the step of discontinuously detecting comprises the step of periodically illuminating the object during successive periods when the object is imaged on the TDI detector, each period being substantially less than the time required for the output signal to diverge by more than a pixel away from the image of the object on the TDI detector.

8. The method of claim 1, further comprising the step of clocking the output signal at a rate that that ensures the velocity of the output signal propagating over the TDI detector is defined so that a successive image of the object formed on the TDI detector does not overlap the output signal for a previous image of the object.

9. The method of claim 1, further comprising the step of operating in a synchronous mode in which the velocity of the image of the object on the TDI detector and the velocity of the output signal propagating over the TDI detector are substantially equal, for a different portion of the time during which the output signal is propagating over the TDI detector.

10. The method of claim 9, further comprising the steps of:

(a) operating in the synchronous mode while an image of the object is formed on the TDI detector;

(b) preventing detection of the light from the object by the TDI detector for a period of time;

(c) operating in the asynchronous mode during said period of time, the velocity with which the output signal propagates over the TDI detector being different during the asynchronous mode than during the synchronous mode; and (d) again operating in the synchronous mode while a subsequent image of the object is formed on the TDI detector, said output signal propagating away from the subsequent image during while operating in the asynchronous mode sufficiently to avoid overlapping the subsequent image that is formed on the TDI detector.

11. The method of claim 10, wherein the output signal is propagated out of the TDI detector before a subsequent image of an object is formed on the TDI detector.

12. The method of claim 11, wherein the subsequent image is formed of a different object, the output signal for a previous object being propagated out of the TDI detector to avoid crosstalk between the output signal for the previous object and the output signal for the subsequent object.

13. The method of claim 10, wherein the light from the object periodically reaches the TDI detector, further comprising the step of controlling a timing during which the light reaches the TDI detector and the velocity with which the output signal propagates over the TDI detector in concert to produce a desired kinetic measurement period, so that changing characteristics of the object over the desired measurement period are apparent in the output signal from the TDI detector.

14. A system for producing an output signal usable to determine at least one characteristic of an object as a function of an image of the object, comprising:

(a) a TDI detector that produces an output signal indicative of said at least one characteristic of the object; and (b) an optical element disposed to receive light from an object, forming the image of the object on the TDI detector, said TDI detector producing the output signal that propagates over the TDI detector with a velocity that is substantially different than a velocity with which the image propagates over the TDI detector for at least part of a time during which the output signal is propagating over the TDI detector.

15. The system of claim 14, further comprising a light source that illuminates the object.

16. The system of claim 15, wherein the light source is periodically pulsed to illuminate the object with pulses of light, pulses of light from the object forming a plurality of images of the object on the TDI detector, said images being spaced apart by at least a dimension of each image to avoid overlap between the plurality of images.

17. The system of claim 15, further comprising one of a gate and a shutter that is disposed in one of two locations, including between the light source and the object, and between the object and the TDI detector, said one of the gate and the shutter being periodically actuated to enable a plurality of images of the object to be formed on the TDI detector, said images being spaced apart by at least a dimension of each image to substantially avoid overlap between the plurality of images.

18. The system of claim 14, further comprising one of a gate and a shutter that is disposed between the object and the TDI detector, said one of the gate and the shutter being periodically actuated to enable a plurality of images of the object to be formed on the TDI detector, said images being spaced apart by at least a dimension of each image to substantially avoid overlap between the plurality of images.

19. The system of claim 14, wherein the object emits light, further comprising one of a gate and a shutter that is disposed between the object and the TDI detector, said one of the gate and the shutter being periodically actuated to enable a plurality of images of the object to be formed on the TDI detector, said images being spaced apart by at least a dimension of each image to substantially avoid overlap between the plurality of images.

20. The system of claim 14, further comprising means for determining a characteristic of the object as a function of the output signal produced by the TDI detector.

21. The system of claim 14, wherein the output signal initially propagates over the TDI detector in synchronization with an initial image of the object for a first period of time, and then propagates over the TDI detector asynchronously and independent of any image of the object for a second period of time.

22. The system of claim 21, wherein a subsequent image of the object is formed on the TDI detector after the output signal for the initial image of the object has propagated over the TDI detector sufficiently so as to not overlap the output signal for the subsequent image, and wherein the output signal for the initial image and the output signal for the subsequent image then propagate over the TDI detector in synchronization with the subsequent image for a third period of time.

23. The system of claim 21, wherein a subsequent image of a different object is formed on the TDI detector after the output signal for the initial image has propagated from the TDI detector, thereby substantially avoiding crosstalk between the output signal for the initial image and the output signal for the subsequent image.

24. A system for producing an output signal corresponding to an image of an object, comprising:

(a) a time delay integration (TDI) detector that is responsive to light from the object, producing a signal corresponding thereto; and (b) an optical element that directs light from the object onto the TDI detector, producing an image on the TDI detector for which the TDI detector produces a corresponding output signal, said image moving over the TDI detector at a first velocity, and said output signal propagating over the TDI detector at a second velocity that is different than the first velocity for at least a portion of the time during which the output signal remains on the TDI detector.

25. The system of claim 24, wherein one of the first velocity and the second velocity is substantially equal to zero.

26. The system of claim 24, wherein the image of the object is blurred as a result of differences between the first velocity and the second velocity over time.

27. The system of claim 26, wherein further comprising means for distinguishing one of a wavelength, a waveband, a phase, and a polarization of the light from the object.

28. The system of claim 25, further comprising a pulsating light source that illuminates the object so that the light from the object periodically forms an image of the object on the TDI detector, producing a succession of images of the object and a corresponding succession of output signals, each successive output signal corresponding to a different image of the object.

29. The system of claim 28, wherein the pulsating light source pulses at a rate such that a successive image does not overlap an output signal corresponding to a previous image on the TDI detector.

30. The system of claim 25, further comprising one of a gate and a shutter that periodically interrupts light used to form successive images of the object on the TDI detector, a time interval in which said one of the gate and the shutter is activated to enable to form successive images being selected so that each successive image is spaced apart from the output signal corresponding to a previous image sufficiently to avoid overlapping said output signal.

31. The system of claim 25, wherein the output signal corresponding to the image propagates over the TDI detector in synchrony with the image for at least a portion of the time during which the output signal is on the TDI detector.

32. The system of claim 31, wherein successive images of an object are formed on the TDI detector with light from the object, at spaced apart times, an output signal corresponding to an image being formed propagating over the TDI detector in synchronization with the image formed for a first period of time and then being driven to propagate over the TDI at a different velocity before a successive image is formed so that an output signal corresponding to the successive image does not overlap the output signal corresponding to the image.

33. The system of claim 31, wherein images of different objects are successively formed on the TDI detector with light from the different objects, at spaced apart times, an output signal corresponding to an image of an object that is being formed propagating over the TDI detector in synchronization with the image that is being formed for a first period of time and then being clocked to propagate out of the TDI detector at a different velocity before a successive image of a different object is formed so that an output signal corresponding to the successive image does not overlap the output signal corresponding to the image.

* * * * *